United States Patent
Riesner (12)

(10) Patent No.: US 10,138,651 B1
(45) Date of Patent: Nov. 27, 2018

(54) WINTER TANNING TENT

(71) Applicant: William Riesner, Finksburg, MD (US)

(72) Inventor: William Riesner, Finksburg, MD (US)

(*) Notice: Subject to any disclaimer, the term of this patent is extended or adjusted under 35 U.S.C. 154(b) by 205 days.

(21) Appl. No.: 15/340,256

(22) Filed: Nov. 1, 2016

(51) Int. Cl.
| | | |
|---|---|---|
| *E04H 15/34* | (2006.01) | |
| *E04H 15/54* | (2006.01) | |
| *E04H 15/64* | (2006.01) | |
| *A61N 5/06* | (2006.01) | |
| *E04H 15/00* | (2006.01) | |
| *E04H 1/12* | (2006.01) | |

(52) U.S. Cl.
CPC ......... *E04H 15/003* (2013.01); *A61N 5/0614* (2013.01); *E04H 15/34* (2013.01); *E04H 15/54* (2013.01); *E04H 15/64* (2013.01); *E04H 2001/1288* (2013.01)

(58) Field of Classification Search
CPC .............................. E04H 15/003; A61N 5/0614
See application file for complete search history.

(56) References Cited

U.S. PATENT DOCUMENTS

| | | | | |
|---|---|---|---|---|
| 1,617,435 A | * | 2/1927 | Coleman | ............... E04H 15/003 135/158 |
| 1,780,363 A | * | 11/1930 | Proctor | ................. E04H 15/003 607/95 |
| 2,118,474 A | * | 5/1938 | Whitton | ................ E04H 15/003 135/115 |
| 3,244,186 A | | 4/1966 | Thomason | |
| 3,498,587 A | * | 3/1970 | Friedberg | .................. E04H 1/12 5/512 |
| 3,610,249 A | * | 10/1971 | Baker | ................... E04H 15/003 16/265 |
| 4,320,744 A | * | 3/1982 | Fodor | ........................ F24J 2/36 126/570 |
| 4,497,145 A | * | 2/1985 | Louwenaar | ........... E04H 15/003 126/628 |
| D279,313 S | | 6/1985 | Tolley | |
| 4,525,884 A | | 7/1985 | Tolley | |
| 4,719,935 A | * | 1/1988 | Gustafson | ............... E04H 15/10 135/124 |
| 5,010,909 A | * | 4/1991 | Cleveland | ............. E04H 15/001 135/119 |
| 5,085,212 A | * | 2/1992 | DeCosta | ............... E04H 15/003 4/526 |

(Continued)

FOREIGN PATENT DOCUMENTS

CA    2502989 A1    8/2006

*Primary Examiner* — David R Dunn
*Assistant Examiner* — Danielle Jackson
(74) *Attorney, Agent, or Firm* — Kyle A. Fletcher, Esq.

(57) ABSTRACT

The winter tanning tent is a structure that comprises a shell, a frame, and a floor panel. The frame is a structure upon which the shell is mounted such that a protected interior space is created. The shell is substantially formed from a transparent material such that sunlight will pass through the shell into the interior space formed by the shell thereby heating the interior space. The frame is mounted on a floor panel such that a person standing within the interior space is protected from the supporting surface upon which the winter tanning tent is placed. The floor panel comprises a plate like structure that is placed on the supporting surface. The purpose of the winter tanning tent is to create a space warmed by solar energy that can be used for sunbathing purposes on uncomfortably cool days.

17 Claims, 4 Drawing Sheets

(56) References Cited

U.S. PATENT DOCUMENTS

| | | | |
|---|---|---|---|
| 5,088,514 A * | 2/1992 | House | E04H 15/58 |
| | | | 135/139 |
| 5,446,580 A * | 8/1995 | Collins | E04H 15/003 |
| | | | 135/117 |
| 5,733,314 A | 3/1998 | Perrino | |
| 5,837,000 A | 11/1998 | Boudreau | |
| 6,585,751 B1 | 7/2003 | Silverman | |
| 8,365,752 B1 | 2/2013 | Fortin | |
| 9,447,602 B1 * | 9/2016 | Arias | E04H 15/58 |
| 2011/0319970 A1 | 12/2011 | Elliott | |

* cited by examiner

WINTER TANNING TENT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of building including tents and canopies, more specifically, a part component or construction detail for a tent.

SUMMARY OF INVENTION

The winter tanning tent is a structure that comprises a shell, a frame, and a floor panel. The frame is a structure upon which the shell is mounted such that a protected interior space is created. The shell is substantially formed from a transparent material such that sunlight will pass through the shell into the interior space formed by the shell thereby heating the interior space. The frame is mounted on a floor panel such that a person standing within the interior space is protected from the supporting surface upon which the winter tanning tent is placed. The floor panel comprises a plate like structure that is placed on the supporting surface. The purpose of the winter tanning tent is to create a space warmed by solar energy that can be used for sunbathing purposes on uncomfortably cool days.

These together with additional objects, features and advantages of the winter tanning tent will be readily apparent to those of ordinary skill in the art upon reading the following detailed description of the presently preferred, but nonetheless illustrative, embodiments when taken in conjunction with the accompanying drawings.

In this respect, before explaining the current embodiments of the winter tanning tent in detail, it is to be understood that the winter tanning tent is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the winter tanning tent.

It is therefore important that the claims be regarded as including such equivalent construction insofar as they do not depart from the spirit and scope of the winter tanning tent. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
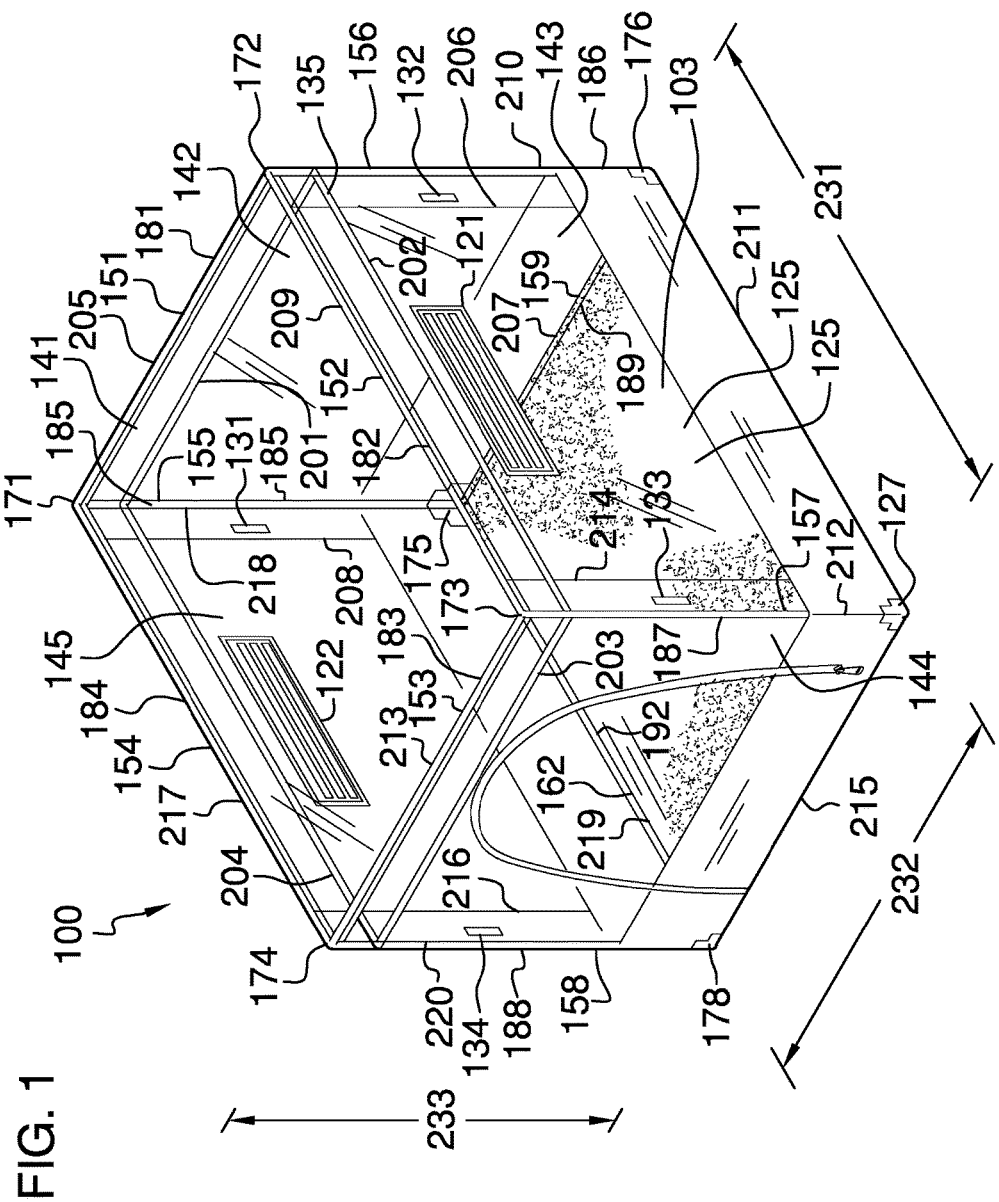
FIG. 1 is a perspective view of an embodiment of the disclosure.
Figure 2:
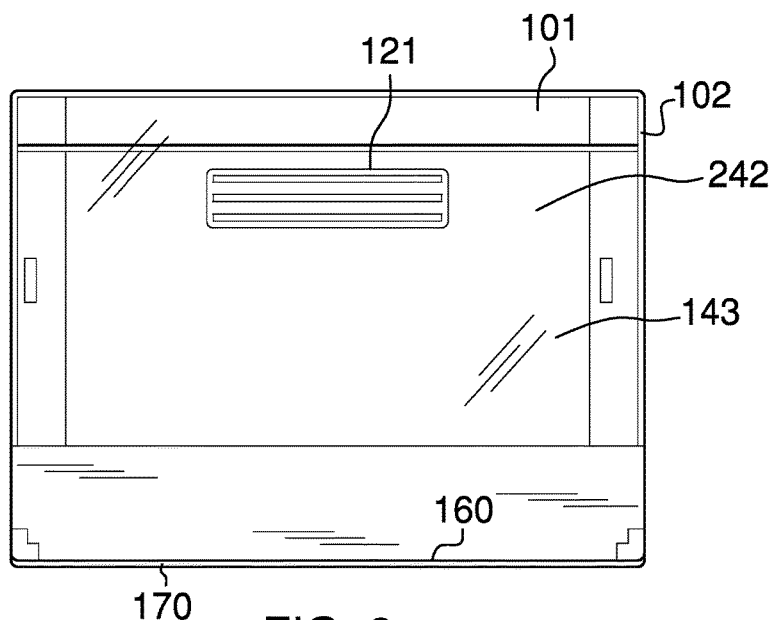
FIG. 2 is a side view of an embodiment of the disclosure.
Figure 3:
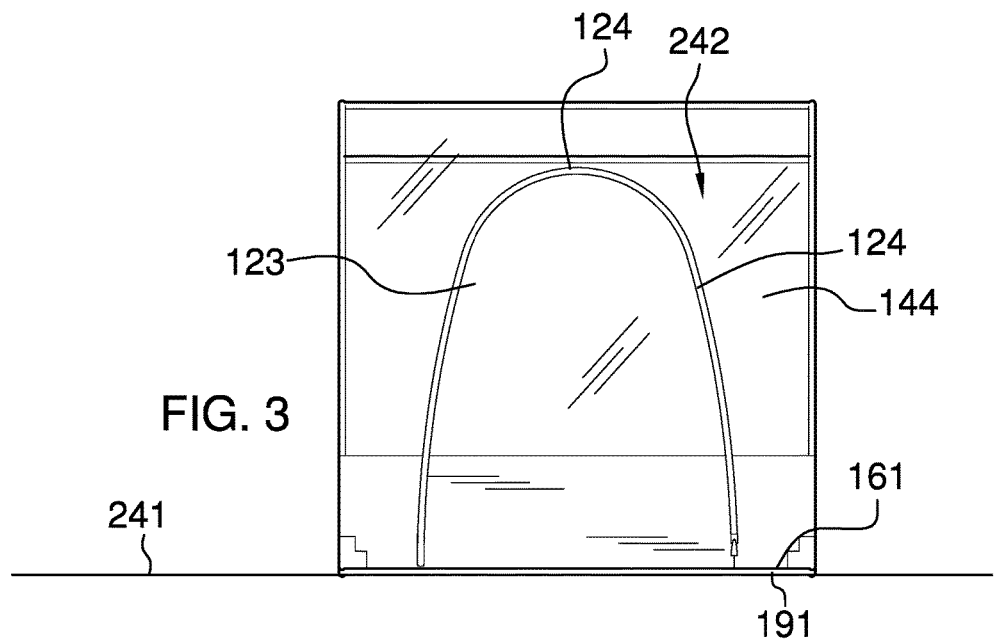
FIG. 3 is a front view of an embodiment of the disclosure.
Figure 4:
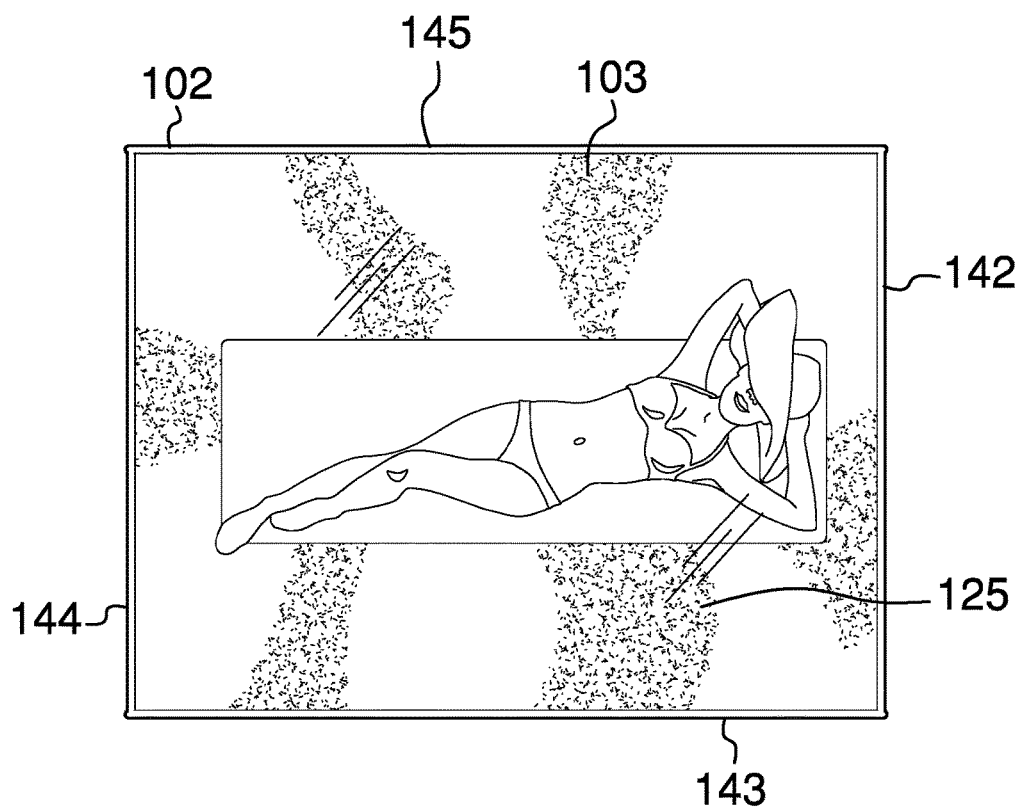
FIG. 4 is a top view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 6.

The winter tanning tent 100 (hereinafter invention) is a structure that comprises a shell 101, a frame 102, and a floor panel 103. The frame 102 is a structure upon which the shell 101 is mounted such that a protected interior space 242 is created. The shell 101 is substantially formed from a transparent material such that sunlight will pass through the shell 101 into the interior space 242 formed by the shell 101 thereby heating the interior space 242. The frame 102 is mounted on a floor panel 103 such that a person standing within the interior space 242 is protected from the supporting surface 241 upon which the invention 100 is placed. The floor panel 103 comprises a commercially available plate like structure that is used as a covering on the supporting surface 241. The purpose of the invention 100 is to create an interior space 242 warmed by solar energy that can be used for sunbathing purposes on uncomfortably cool days.

The shell 101 comprises a first panel 141, a second panel 142, a third panel 143, a fourth panel 144, and a fifth panel 145. The first panel 141 is a sheeting that is cut in a rectangular shape. The first panel 141 that is further defined with a length 231, a width 232 and a height 233. The second panel 142 is a sheeting that is cut in a rectangular shape. The second panel 142 that is further defined with the length 231, the width 232 and the height 233. The third panel 143 is a sheeting that is cut in a rectangular shape. The third panel 143 that is further defined with the length 231, the width 232 and the height 233. The fourth panel 144 is a sheeting that is cut in a rectangular shape. The fourth panel 144 that is further defined with the length 231, the width 232 and the height 233. The fifth panel 145 is a sheeting that is cut in a rectangular shape. The fifth panel 145 that is further defined with the length 231, the width 232 and the height 233. The directions of the length 231, the width 232, and the height 233 are determined relative to the frame 102 and are explicitly identified elsewhere in this disclosure.

The first panel 141 is further defined with a first edge 201, a second edge 202, a third edge 203, and a fourth edge 204. The second panel 142 is further defined with a fifth edge 205, a sixth edge 206, a seventh edge 207, and an eighth edge 208. The third panel 143 is further defined with a ninth edge 209, a tenth edge 210, an eleventh edge 211, and a twelfth edge 212. The fourth panel 144 is further defined with a thirteenth edge 213, a fourteenth edge 214, a fifteenth edge 215, and a sixteenth edge 216. The fifth panel 145 is further defined with a seventeenth edge 217, an eighteenth edge 218, a nineteenth edge 219, and a twentieth edge 220. The relative spans of a selection of the edges discussed in this paragraph are described elsewhere in this disclosure.

The first panel 141 is formed from a first transparent plastic sheeting cut in a rectangle shape.

The second panel 142 is formed from a second transparent plastic sheeting cut in a rectangle shape. A rectangular region of the second panel 142 is blacked out such that the blacked out rectangular region will collect solar energy and convert the solar energy into radiant heat within the structure. The rectangular region of the second panel 142 is bounded by: the sixth edge 206, the seventh edge 207, the eighth edge 208, from the seventh edge 207 to a point one third of the distance of the span between the fifth edge 205 and the seventh edge 207.

The third panel 143 is formed from a third transparent plastic sheeting cut in a rectangle shape. A rectangular region of the third panel 143 is blacked out such that the blacked out rectangular region will collect solar energy and convert the solar energy into radiant heat within the structure. The rectangular region of the third panel 143 is bounded by: the tenth edge 210, the eleventh edge 211, the twelfth edge 212, and from the eleventh edge 211 to a point one third of the distance of the span between the ninth edge 209 and the eleventh edge 211.

The fourth panel 144 is formed from a fourth transparent plastic sheeting cut in a rectangle shape. A rectangular region of the fourth panel 144 is blacked out such that the blacked out rectangular region will collect solar energy and convert the solar energy into radiant heat within the structure. The rectangular region of the fourth panel 144 is bounded by: the fourteenth edge 214, the fifteenth edge 215, the sixteenth edge 216, and from the fifteenth edge 215 to a point one third of the distance of the span between the thirteenth edge 213 and the fifteenth edge 215.

The fifth panel 145 is formed from a fifth transparent plastic sheeting cut in a rectangle shape. A rectangular region of the fifth panel 145 is blacked out such that the blacked out rectangular region will collect solar energy and convert the solar energy into radiant heat within the structure. The rectangular region of the fifth panel 145 is bounded by: the eighteenth edge 218, the nineteenth edge 219, the twentieth edge 220, and from the nineteenth edge 219 to a point one third of the distance of the span between the seventeenth edge 217 and the nineteenth edge 219.

The fifth edge 205 of the second panel 142 is folded back upon itself and using a seam selected from a plurality of seams 136 is joined to the second panel 142 to form a first sleeve 181. The ninth edge 209 of the third panel 143 is folded back upon itself and using a seam selected from the plurality of seams 136 is joined to the third panel 143 to form a second sleeve 182. The thirteenth edge 213 of the fourth panel 144 is folded back upon itself and using a seam selected from the plurality of seams 136 is joined to the fourth panel 144 to form a third sleeve 183. The seventeenth edge 217 of the fifth panel 145 is folded back upon itself and using a seam selected from the plurality of seams 136 is joined to the fifth panel 145 to form a fourth sleeve 184.

The eighteenth edge 218 of the fifth panel 145 is folded back upon itself and using a seam selected from the plurality of seams 136 is joined to the fifth panel 145 to form a fifth sleeve 185. The tenth edge 210 of the third panel 143 is folded back upon itself and using a seam selected from the plurality of seams 136 is joined to the third panel 143 to form a sixth sleeve 186. The twelfth edge 212 of the third panel 143 is folded back upon itself and using a seam selected from the plurality of seams 136 is joined to the third panel 143 to form a seventh sleeve 187. The twentieth edge 220 of the fifth panel 145 is folded back upon itself and using a seam selected from the plurality of seams 136 is joined to the fifth panel 145 to form a eighth sleeve 188. The seventh edge 207 of the second panel 142 is folded back upon itself and using a seam selected from the plurality of seams 136 is joined to the second panel 142 to form a ninth sleeve 189. The eleventh edge 211 of the third panel 143 is folded back upon itself and using a seam selected from the plurality of seams 136 is joined to the third panel 143 to form a tenth sleeve 190. The fifteenth edge 215 of the fourth panel 144 is folded back upon itself and using a seam selected from the plurality of seams 136 is joined to the fourth panel 144 to form a eleventh sleeve 191. The nineteenth edge 219 of the fifth panel 145 is folded back upon itself and using a seam selected from the plurality of seams 136 is joined to the fifth panel 145 to form a twelfth sleeve 192. Each sleeve described in this paragraph is a tubular channel formed within the associated panel that is sized to receive a pole described elsewhere in this disclosure.

The first panel 141 further comprises a readily and commercially available elastic webbing 135. The elastic webbing 135 is attached while under tension to the first edge 201, the second edge 202, the third edge 203, and the fourth edge 204 of the first panel 141. In the first potential embodiment of the disclosure, the elastic webbing 135 attaches to the first panel 141 using an adhesive.

Figure 5:
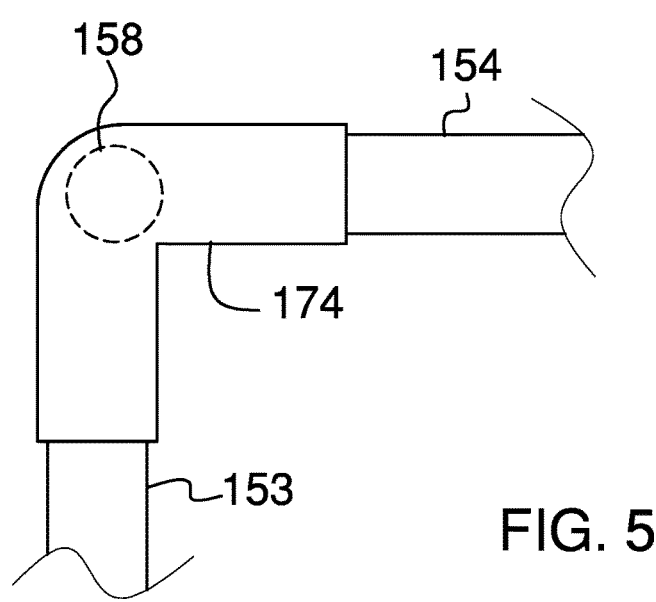
FIG. 5 is a detail view of an embodiment of the disclosure.
Figure 6:
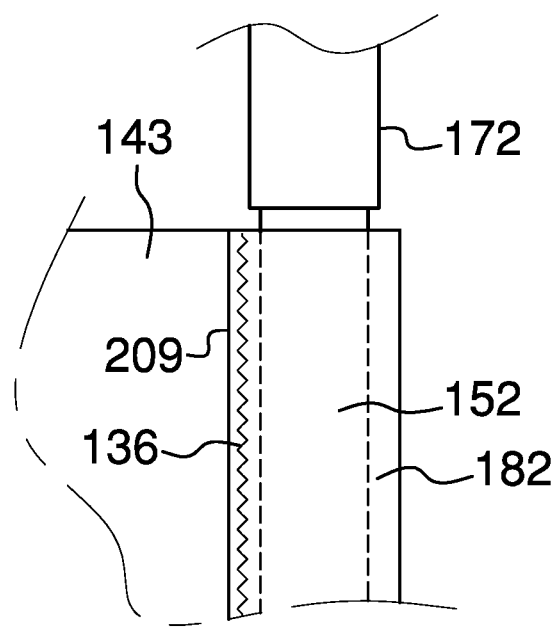
FIG. 6 is a detail view of an embodiment of the disclosure.

The frame 102 is a rectangular block structure that comprises a first pole 151, a second pole 152, a third pole 153, a fourth pole 154, a fifth pole 155, a sixth pole 156, a seventh pole 157, an eighth pole 158, a ninth pole 159, a tenth pole 160, an eleventh pole 161, a twelfth pole 162, a first side outlet elbow 171, a second side outlet elbow 172, a third side outlet elbow 173, a fourth side outlet elbow 174, a fifth side outlet elbow 175, a sixth side outlet elbow 176, a seventh side outlet elbow 177, and an eighth side outlet elbow 178. Each of the poles described in this paragraph is a transparent cylindrical shaft that is preferably made from an acrylic polymer. Each of the side elbow outlets described in this disclosure is a commercially available side elbow outlet. As shown in FIG. 5, a side elbow outlet is a three aperture plumbing (including polyvinylchloride piping) fitting wherein the center axis of any one of the port of the side elbow outlet is perpendicular to the plane formed by the center axes of the remaining two ports.

The length 231 direction is defined as the direction that is parallel to the direction of the second pole 152. The width 232 direction is defined as the direction that is parallel to the direction of the first pole 151. The height 233 direction is defined as the direction that is parallel to the direction of the fifth pole 155. The span of the length 231 of the first panel 141 is greater than the span of the second pole 152. The span of the width 232 of the first panel 141 is greater than the span of the first pole 151. The span of the width 232 of the second panel 142 is greater than the span of the first pole 151. The span of the width 232 of the fourth panel 144 is greater than the span of the first pole 151.

The invention 100 is assembled as described in this paragraph and the following three paragraphs. The first pole 151 is inserted through the first sleeve 181. The second pole 152 is inserted through the second sleeve 182. The third pole 153 is inserted through the third sleeve 183. The fourth pole 154 is inserted through the fourth sleeve 184. The fifth pole 155 is inserted through the fifth sleeve 185. The sixth pole 156 is inserted through the sixth sleeve 186. The seventh pole 157 is inserted through the seventh sleeve 187. The eighth pole 158 is inserted through the eighth sleeve 188. The ninth pole 159 is inserted through the ninth sleeve 189. The tenth pole 160 is inserted through the tenth sleeve 190. The eleventh pole 161 is inserted through the eleventh sleeve 191. The twelfth pole 162 is inserted through the twelfth sleeve 192.

The first side outlet elbow 171 attaches the first pole 151 to the fourth pole 154 and the fifth pole 155 to form a corner of the frame 102. The second side outlet elbow 172 attaches the first pole 151 to the second pole 152 and the sixth pole 156 to form a corner of the frame 102. The third side outlet elbow 173 attaches the second pole 152 to the third pole 153 and the seventh pole 157 to form a corner of the frame 102. The fourth side outlet elbow 174 attaches the fourth pole 154 to the third pole 153 and the eighth pole 158 to form a corner of the frame 102. The fifth side outlet elbow 175 attaches the fifth pole 155 to the ninth pole 159 and the twelfth pole 162 to form a corner of the frame 102. The sixth side outlet elbow 176 attaches the sixth pole 156 to the ninth pole 159 and the tenth pole 160 to form a corner of the frame 102. The seventh side outlet elbow 177 attaches the seventh pole 157 to the tenth pole 160 and the eleventh pole 161 to form a corner of the frame 102. The eighth side outlet elbow 178 attaches the eighth pole 158 to the eleventh pole 161 and the twelfth pole 162 to form a corner of the frame 102.

A first hook and loop fastener 131 attaches the eighth edge 208 of the second panel 142 to the fifth panel 145. A second hook and loop fastener 132 attaches the sixth edge 206 of the second panel 142 to the third panel 143. A third hook and loop fastener 133 attaches the fourteenth edge 214 of the fourth panel 144 to the third panel 143. A fourth hook and loop fastener 134 attaches the sixteenth edge 216 of the fourth panel 144 to the fifth panel 145. Each of the hook and loop fasteners described in this disclosure is a readily and commercially hook and loop fastener that is attached to its associated panels using an adhesive.

As shown most clearly in FIG. 1, the invention 100 is then enclosed by placing the first panel 141 over the top of the invention 100 in such a manner that the elastic webbing 135 of the first panel 141 fits over and wraps around the first pole 151, the second pole 152, the third pole 153, and the fourth pole 154.

The first potential embodiment of the disclosure further comprises: 1) a first vent 121 that is installed in the third panel 143; 2) a second vent 122 that is installed in the fifth panel 145; 3) a door flap 123 that is installed in the fourth panel 144; 4) a zipper 124 that secures the door flap 123 to the fourth panel 144 when in the closed position; and, 5) a carpet 125 that is installed on the surface of the floor panel 103 that is distal from the supporting surface 241. The first vent 121, the second vent 122, the zipper 124, and the carpet 125 are readily and commercially available. The door flap 123 is cut directly into the fourth panel 144. Methods to install zippers and vents in sheetings are well known and documented in the construction arts.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Elastic: As used in this disclosure, an elastic is a material or object that deforms when a force is applied to it and that is able to return to its original shape after the force is removed. A material that exhibits these qualities is also referred to as an elastomeric material.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Fastener: As used in this disclosure, a fastener is a device that is used to join or affix two objects. Fasteners generally comprise a first element, which is attached to the first object and a second element which is attached to the second object such that the first element and the second element join to affix the first object and the second object. Common fasteners include, but are not limited to, zippers, snaps, buttons, buckles, quick release buckles, or hook and loop fasteners.

Flap: As used in this disclosure, a flap is a piece of material that is hinged or otherwise attached to a surface using one side such that the piece of material hangs in such a way as to cover a hole in the surface.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook or loop surface" with the understanding that when the two objects are fastened together one of the two objects will have a hook surface and the remaining object will have the loop surface.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, or an ultrasonically bonded seam.

Shaft: As used in this disclosure, the term shaft is used to describe a rigid cylinder structure. The terms inner diameter of the shaft and outer diameter of the shaft are used as they would be used by those skilled in the plumbing arts. The definition of shaft explicitly includes solid shafts or shafts that are formed more like pipes with a hollow passage through the shaft that runs along the center axis of the shaft cylinder.

Sheeting: As used in this disclosure, sheeting is a material, such as a textile, a plastic, or a metal foil, in the form of a thin flexible layer or layers.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

Zipper: As used in this disclosure, a zipper is a fastening device comprising two flexible strips with interlocking components that are opened and closed by pulling a slide along the two flexible strips.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A tent comprising:
a shell, a frame, and a floor panel;
wherein the frame is a structure upon which the shell is mounted such that an interior space is created;
wherein the shell comprises a transparent material such that sunlight will pass through the shell into the interior space, wherein the interior space is warmed by solar energy;
wherein the frame is mounted on the floor panel;
wherein the shell comprises a first panel, a second panel, a third panel, a fourth panel, and a fifth panel;
wherein the tent is further defined with a length, a width and a height;
wherein the first panel is a sheeting that is cut in a rectangular shape;
wherein the second panel is a sheeting that is cut in a rectangular shape;
wherein the third panel is a sheeting that is cut in a rectangular shape;
wherein the fourth panel is a sheeting that is cut in a rectangular shape;
wherein the fifth panel is a sheeting that is cut in a rectangular shape;
wherein the first panel is further defined with a first edge, a second edge, a third edge, and a fourth edge;
wherein the second panel is further defined with a fifth edge, a sixth edge, a seventh edge, and an eighth edge;
wherein the third panel is further defined with a ninth edge, a tenth edge, an eleventh edge, and a twelfth edge;
wherein the fourth panel is further defined with a thirteenth edge, a fourteenth edge, a fifteenth edge, and a sixteenth edge;
wherein the fifth panel is further defined with a seventeenth edge, an eighteenth edge, a nineteenth edge, and a twentieth edge;
wherein a first rectangular region of the second panel is blacked out;
wherein the first rectangular region of the second panel is bounded by: the sixth edge, the seventh edge, the eighth edge, from the seventh edge to a point one third of the distance of the span between the fifth edge and the seventh edge;
wherein a second rectangular region of the third panel is blacked out;
wherein the second rectangular region of the third panel is bounded by: the tenth edge, the eleventh edge, the twelfth edge, and from the eleventh edge to a point one third of the distance of the span between the ninth edge and the eleventh edge;
wherein a third rectangular region of the fourth panel is blacked out;
wherein the third rectangular region of the fourth panel is bounded by:
the fourteenth edge, the fifteenth edge, the sixteenth edge, and from the fifteenth edge to a point one third of the distance of the span between the thirteenth edge and the fifteenth edge;
wherein a fourth rectangular region of the fifth panel is blacked out;
wherein the fourth rectangular region of the fifth panel is bounded by:
the eighteenth edge, the nineteenth edge, the twentieth edge, and from the nineteenth edge to a point one third of the distance of the span between the seventeenth edge and the nineteenth edge.

2. The tent according to claim 1
wherein the fifth edge of the second panel is folded back upon itself and using a seam selected from a plurality of seams is joined to the second panel to form a first sleeve;
wherein the ninth edge of the third panel is folded back upon itself and using a seam selected from the plurality of seams is joined to the third panel to form a second sleeve;
wherein the thirteenth edge of the fourth panel is folded back upon itself and using a seam selected from the plurality of seams is joined to the fourth panel to form a third sleeve;
wherein the seventeenth edge of the fifth panel is folded back upon itself and using a seam selected from the plurality of seams is joined to the fifth panel to form a fourth sleeve;
wherein the eighteenth edge of the fifth panel is folded back upon itself and using a seam selected from the plurality of seams is joined to the fifth panel to form a fifth sleeve;
wherein the tenth edge of the third panel is folded back upon itself and using a seam selected from the plurality of seams is joined to the third panel to form a sixth sleeve;
wherein the twelfth edge of the third panel is folded back upon itself and using a seam selected from the plurality of seams is joined to the third panel to form a seventh sleeve;
wherein the twentieth edge of the fifth panel is folded back upon itself and using a seam selected from the plurality of seams is joined to the fifth panel to form a eighth sleeve;
wherein the seventh edge of the second panel is folded back upon itself and using a seam selected from the plurality of seams is joined to the second panel to form a ninth sleeve;

wherein the eleventh edge of the third panel is folded back upon itself and using a seam selected from the plurality of seams is joined to the third panel to form a tenth sleeve;
wherein the fifteenth edge of the fourth panel is folded back upon itself and using a seam selected from the plurality of seams is joined to the fourth panel to form a eleventh sleeve;
wherein the nineteenth edge of the fifth panel is folded back upon itself and using a seam selected from the plurality of seams is joined to the fifth panel to form a twelfth sleeve;
wherein each sleeve is a tubular channel formed within the associated panel.

3. The tent according to claim 2
wherein the first panel further comprises an elastic webbing;
wherein the elastic webbing is attached while under tension to the first edge, the second edge, the third edge, and the fourth edge of the first panel.

4. The tent according to claim 3
wherein the frame is a rectangular block structure that comprises a first pole, a second pole, a third pole, a fourth pole, a fifth pole, a sixth pole, a seventh pole, an eighth pole, a ninth pole, a tenth pole, an eleventh pole, a twelfth pole, a first side outlet elbow, a second side outlet elbow, a third side outlet elbow, a fourth side outlet elbow, a fifth side outlet elbow, a sixth side outlet elbow, a seventh side outlet elbow, and an eighth side outlet elbow;
wherein each of the poles is a transparent cylindrical shaft;
wherein each side elbow outlet is a three aperture fitting wherein the center axis of any one of the port of the side elbow outlet is perpendicular to the plane formed by the center axes of the remaining two ports;
wherein the length direction is further defined as the direction that is parallel to the direction of the second pole;
wherein the width direction is further defined as the direction that is parallel to the direction of the first pole;
wherein the height direction is further defined as the direction that is parallel to the direction of the fifth pole.

5. The tent according to claim 4 wherein the span of the length of the first panel is greater than the span of the second pole;
wherein the span of the width of the first panel is greater than the span of the first pole.

6. The tent according to claim 5
wherein the span of the width of the second panel is greater than the span of the first pole;
wherein the span of the width of the fourth panel is greater than the span of the first pole.

7. The tent according to claim 6 wherein the first pole is inserted through the first sleeve;
wherein the second pole is inserted through the second sleeve;
wherein the third pole is inserted through the third sleeve;
wherein the fourth pole is inserted through the fourth sleeve;
wherein the fifth pole is inserted through the fifth sleeve;
wherein the sixth pole is inserted through the sixth sleeve;
wherein the seventh pole is inserted through the seventh sleeve;
wherein the eighth pole is inserted through the eighth sleeve;
wherein the ninth pole is inserted through the ninth sleeve;
wherein the tenth pole is inserted through the tenth sleeve;
wherein the eleventh pole is inserted through the eleventh sleeve;
wherein the twelfth pole is inserted through the twelfth sleeve.

8. The tent according to claim 7
wherein the first side outlet elbow attaches the first pole to the fourth pole and the fifth pole to form a corner of the frame;
wherein the second side outlet elbow attaches the first pole to the second pole and the sixth pole to form a corner of the frame;
wherein the third side outlet elbow attaches the second pole to the third pole and the seventh pole to form a corner of the frame;
wherein the fourth side outlet elbow attaches the fourth pole to the third pole and the eighth pole to form a corner of the frame;
wherein the fifth side outlet elbow attaches the fifth pole to the ninth pole and the twelfth pole to form a corner of the frame;
wherein the sixth side outlet elbow attaches the sixth pole to the ninth pole and the tenth pole to form a corner of the frame;
wherein the seventh side outlet elbow attaches the seventh pole to the tenth pole and the eleventh pole to form a corner of the frame;
wherein the eighth side outlet elbow attaches the eighth pole to the eleventh pole and the twelfth pole to form a corner of the frame.

9. The tent according to claim 8
wherein a first hook and loop fastener attaches the eighth edge of the second panel to the fifth panel;
wherein a second hook and loop fastener attaches the sixth edge of the second panel to the third panel;
wherein a third hook and loop fastener attaches the fourteenth edge of the fourth panel to the third panel;
wherein a fourth hook and loop fastener attaches the sixteenth edge of the fourth panel to the fifth panel.

10. The tent according to claim 9 wherein the tent is enclosed by placing the first panel over the top of the tent in such a manner that the elastic webbing of the first panel fits over and wraps around the first pole, the second pole, the third pole, and the fourth pole.

11. The tent according to claim 10
wherein a first vent that is installed in the third panel;
wherein a second vent that is installed in the fifth panel;
wherein a door flap that is installed in the fourth panel;
wherein a zipper that secures the door flap to the fourth panel;
wherein a carpet that is installed on a surface of the floor panel that is distal from a supporting surface;
wherein the door flap is cut directly into the fourth panel.

12. The tent according to claim 11 wherein the elastic webbing attaches to the first panel using an adhesive;
wherein each of the poles is made from an acrylic polymer.

13. The tent according to claim 1
wherein the frame is a rectangular block structure that comprises a first pole, a second pole, a third pole, a fourth pole, a fifth pole, a sixth pole, a seventh pole, an eighth pole, a ninth pole, a tenth pole, an eleventh pole, a twelfth pole, a first side outlet elbow, a second side outlet elbow, a third side outlet elbow, a fourth side outlet elbow, a fifth side outlet elbow, a sixth side outlet elbow, a seventh side outlet elbow, and an eighth side outlet elbow;
wherein each of the poles is a transparent cylindrical shaft;
wherein each side elbow outlet is a three aperture fitting wherein the center axis of any one of the port of the side elbow outlet is perpendicular to the plane formed by the center axes of the remaining two ports;
wherein the length direction is further defined as the direction that is parallel to the direction of the second pole;
wherein the width direction is further defined as the direction that is parallel to the direction of the first pole;
wherein the height direction is further defined as the direction that is parallel to the direction of the fifth pole.

14. The tent according to claim 13
wherein the fifth edge of the second panel is folded back upon itself and using a seam selected from a plurality of seams is joined to the second panel to form a first sleeve;
wherein the ninth edge of the third panel is folded back upon itself and using a seam selected from the plurality of seams is joined to the third panel to form a second sleeve;
wherein the thirteenth edge of the fourth panel is folded back upon itself and using a seam selected from the plurality of seams is joined to the fourth panel to form a third sleeve;
wherein the seventeenth edge of the fifth panel is folded back upon itself and using a seam selected from the plurality of seams is joined to the fifth panel to form a fourth sleeve;
wherein the eighteenth edge of the fifth panel is folded back upon itself and using a seam selected from the plurality of seams is joined to the fifth panel to form a fifth sleeve;
wherein the tenth edge of the third panel is folded back upon itself and using a seam selected from the plurality of seams is joined to the third panel to form a sixth sleeve;
wherein the twelfth edge of the third panel is folded back upon itself and using a seam selected from the plurality of seams is joined to the third panel to form a seventh sleeve;
wherein the twentieth edge of the fifth panel is folded back upon itself and using a seam selected from the plurality of seams is joined to the fifth panel to form a eighth sleeve;
wherein the seventh edge of the second panel is folded back upon itself and using a seam selected from the plurality of seams is joined to the second panel to form a ninth sleeve;
wherein the eleventh edge of the third panel is folded back upon itself and using a seam selected from the plurality of seams is joined to the third panel to form a tenth sleeve;
wherein the fifteenth edge of the fourth panel is folded back upon itself and using a seam selected from the plurality of seams is joined to the fourth panel to form a eleventh sleeve;
wherein the nineteenth edge of the fifth panel is folded back upon itself and using a seam selected from the plurality of seams is joined to the fifth panel to form a twelfth sleeve;
wherein each sleeve is a tubular channel formed within the associated panel;
wherein the first panel further comprises an elastic webbing;
wherein the elastic webbing is attached while under tension to the first edge, the second edge, the third edge, and the fourth edge of the first panel;
wherein the span of the length direction of the first panel is greater than the span of the second pole;
wherein the span of the width direction of the first panel is greater than the span of the first pole;
wherein the span of the width direction of the second panel is greater than the span of the first pole;
wherein the span of the width direction of the fourth panel is greater than the span of the first pole;
wherein the first pole is inserted through the first sleeve;
wherein the second pole is inserted through the second sleeve;
wherein the third pole is inserted through the third sleeve;
wherein the fourth pole is inserted through the fourth sleeve;
wherein the fifth pole is inserted through the fifth sleeve;
wherein the sixth pole is inserted through the sixth sleeve;
wherein the seventh pole is inserted through the seventh sleeve;
wherein the eighth pole is inserted through the eighth sleeve;
wherein the ninth pole is inserted through the ninth sleeve;
wherein the tenth pole is inserted through the tenth sleeve;
wherein the eleventh pole is inserted through the eleventh sleeve;
wherein the twelfth pole is inserted through the twelfth sleeve;
wherein the first side outlet elbow attaches the first pole to the fourth pole and the fifth pole to form a corner of the frame;
wherein the second side outlet elbow attaches the first pole to the second pole and the sixth pole to form a corner of the frame;
wherein the third side outlet elbow attaches the second pole to the third pole and the seventh pole to form a corner of the frame;
wherein the fourth side outlet elbow attaches the fourth pole to the third pole and the eighth pole to form a corner of the frame;
wherein the fifth side outlet elbow attaches the fifth pole to the ninth pole and the twelfth pole to form a corner of the frame;
wherein the sixth side outlet elbow attaches the sixth pole to the ninth pole and the tenth pole to form a corner of the frame;
wherein the seventh side outlet elbow attaches the seventh pole to the tenth pole and the eleventh pole to form a corner of the frame;
wherein the eighth side outlet elbow attaches the eighth pole to the eleventh pole and the twelfth pole to form a corner of the frame;
wherein a first hook and loop fastener attaches the eighth edge of the second panel to the fifth panel;
wherein a second hook and loop fastener attaches the sixth edge of the second panel to the third panel;
wherein a third hook and loop fastener attaches the fourteenth edge of the fourth panel to the third panel;
wherein a fourth hook and loop fastener attaches the sixteenth edge of the fourth panel to the fifth panel.

15. The tent according to claim 14
wherein the tent is enclosed by placing the first panel over the top of the tent in such a manner that the elastic webbing of the first panel fits over and wraps around the first pole, the second pole, the third pole, and the fourth pole.

16. The tent according to claim 15
wherein a first vent that is installed in the third panel;
wherein a second vent that is installed in the fifth panel;
wherein a door flap that is installed in the fourth panel;
wherein a zipper that secures the door flap to the fourth panel;
wherein a carpet that is installed on a surface of the floor panel that is distal from a supporting surface;
wherein the door flap is cut directly into the fourth panel.

17. The tent according to claim 16
wherein the elastic webbing attaches to the first panel using an adhesive;
wherein each of the poles is made from an acrylic polymer.

\* \* \* \* \*